United States Patent [19]

Woog

[11] Patent Number: 4,595,850
[45] Date of Patent: Jun. 17, 1986

[54] VARIABLE TORQUE MOTOR FOR HYGIENIC APPARATUS

[75] Inventor: Philippe Guy E. Woog, Vesenaz, Switzerland

[73] Assignee: Les Produits Associes LPA SA, Geneva, Switzerland

[21] Appl. No.: 664,614

[22] Filed: Oct. 25, 1984

Related U.S. Application Data

[63] Continuation-in-part of Ser. No. 577,199, Feb. 6, 1984, abandoned.

[51] Int. Cl.[4] .............................................. H02K 7/14
[52] U.S. Cl. .................................... 310/47; 335/207
[58] Field of Search ................... 335/207; 310/47, 50; 318/127, 305; 15/25, 26, 27, 23; 200/19 M

[56] References Cited

U.S. PATENT DOCUMENTS

| | | | |
|---|---|---|---|
| 1,252,897 | 1/1918 | Foster | 318/305 |
| 3,489,936 | 1/1970 | Boyles | 310/47 |
| 3,506,939 | 4/1970 | Hesser et al. | 335/207 |
| 3,559,124 | 1/1971 | Posey | 335/207 |
| 3,609,524 | 9/1971 | Kazmer | 335/207 |
| 4,068,202 | 1/1978 | Lyons, III | 335/207 |
| 4,090,112 | 5/1978 | Selverstone | 310/36 |
| 4,413,199 | 11/1983 | Fischer | 310/50 |

Primary Examiner—Patrick R. Salce
Assistant Examiner—D. L. Rebsch
Attorney, Agent, or Firm—Kane, Dalsimer, Kane, Sullivan and Kurucz

[57] ABSTRACT

A hygienic device comprising an a.c. oscillating motor which has a fixed oscillation rate dependent on the a.c. supply frequency. The amplitude of the oscillations or torque of the motor is varied by varying the power supplied to the motor. The amplitude or torque may be varied in discrete steps by switching different resistors in series with the motor. Reed switches are used to switch the resistors and are mounted obliquely, to facilitate assembly and to reduce the danger of electric shocks to the user.

8 Claims, 9 Drawing Figures

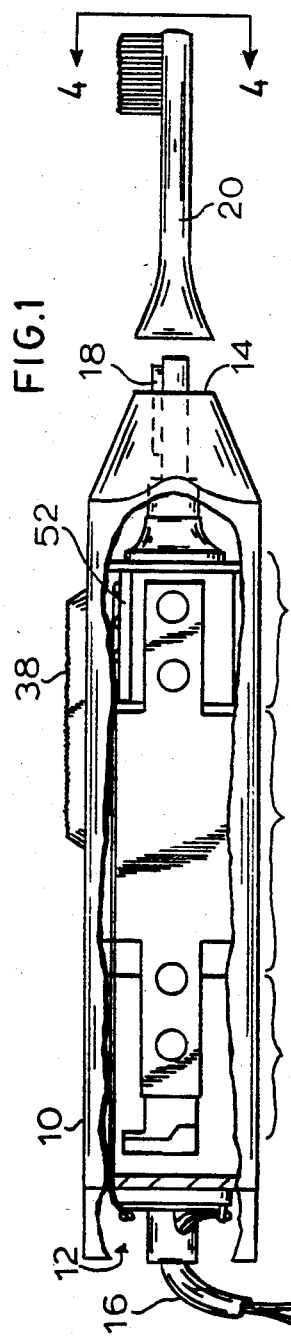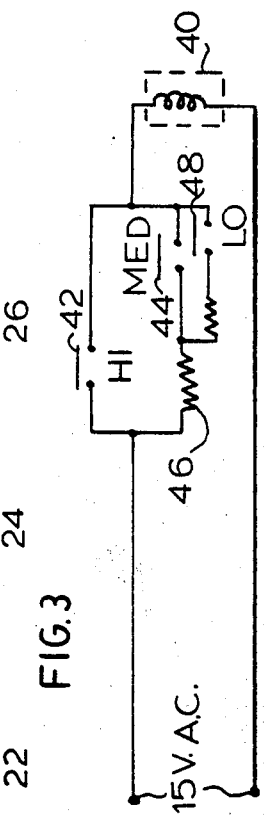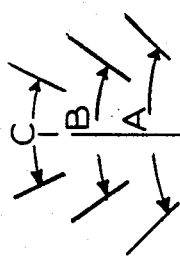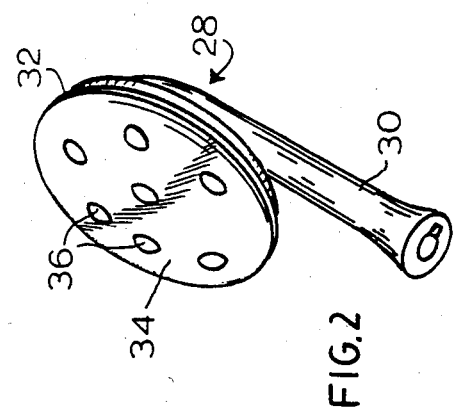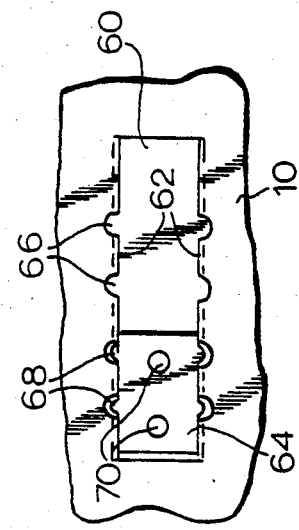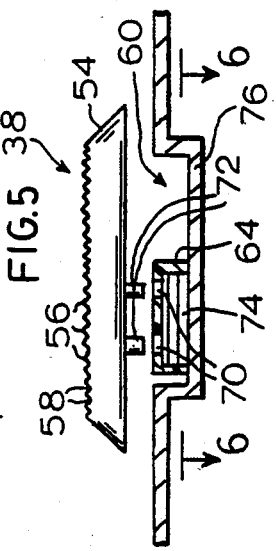

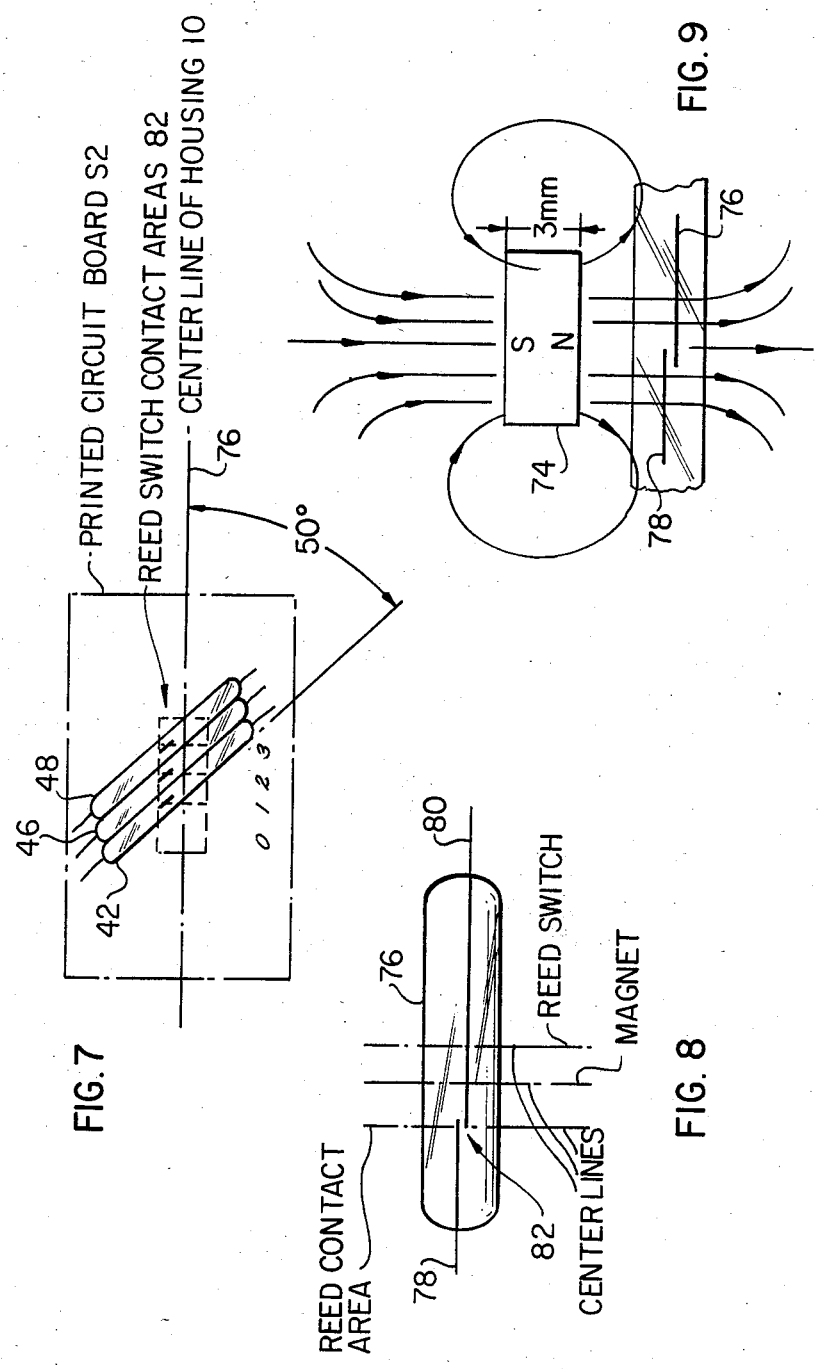

VARIABLE TORQUE MOTOR FOR HYGIENIC APPARATUS

This is a continuation-in-part to U.S. patent application Ser. No. 577,199, filed Feb. 6, 1984, now abandoned.

BACKGROUND OF THE INVENTION

This invention pertains to electrically operated hygienic apparatus such as toothbrushes, face massagers and the like, and more particularly, to a constant-speed variable-torque motor for the same.

In copending, commonly assigned patent application Ser. No. 420,298 filed Sept. 20, 1982, an oscillating a.c. motor is described which is particularly adapted for hygienic devices. More particularly the motor is designed so that its mechanical components are chosen to oscillate at a frequency which is equal to or slightly below the frequency of the a.c. electric power supply. It was found that using this principle stronger motors could be built which occupy relatively smaller spaces. However on further consideration, it was found to be desirable to make the motor with a variable torque and/or angle of operation. For example, if the motor is used in an electric toothbrush, the angle of operation should be varied depending on the age of the user and or other considerations. Inherently small children, persons suffering from periodontitis, or wearers of orthodontic appliances should use the toothbrush at a lower operating angle or torque than normal users. If the motor is used in a hand-held face massager, or skin care treatment device, its angle of operation torque should be varied in accordance with the accessory used and the area of the face or body being treated by the device. For example if a pad is used as an accessory to clean and moisturize skin, a relatively low angle of operation is required for a gentle treatment. On the other hand in general a massaging accessory requires a higher operational angle, except around certain sensitive areas such as the eyes or the forehead.

OBJECTIVES AND SUMMARY OF INVENTION

An objective of the invention is to provide oscillatory electric toothbrush with externally adjustable operational angle.

A further objective is to provide a toothbrush with an externally adjustable output torque.

Another objective is to provide a toothbrush with external controls which are easy to assemble from standard parts and safe to operate. Other objectives and advantages of the invention shall become apparent in the following description of the invention.

According to this invention the torque and/or angle of operation of a constant speed oscillating electric motor is changed by varying the power supplied to the motor. Preferably the means for operating the motor is provided on the motor housing. Preferably the power to the motor is varied in discrete steps by selectively switching various resistors in series with the motor. Reed switches are used for reliability. These reed switches are mounted on the motor while the means for actuating the motor comprises a permanent magnet for operating said reed relays. Thus the housing and motor need no mechanical or electrical interlocking means, thereby insuring that the user will not be exposed to any electrical shocks.

The reed switches are positioned in a preselected arrangement to obtain a relatively small stroke for the activating switch and to insure a proper activation and deactivation of the switches.

BRIEF DESCRIPTION OF THE FIGURES

FIG. 1 shows a complete electric toothbrush in accordance with the invention;

FIG. 2 shows an accessory that could be used as a massaging device when mounted on the device of FIG. 1;

FIG. 3 shows a schematic diagram of the device of FIG. 1;

FIG. 4 shows an end view of the oscillating toothbrush;

FIG. 5 shows a partial sectional side view of the device, illustrating the control switch;

FIG. 6 shows a sectional top view of the control switch;

FIG. 7 shows a top or plan view of the reed switches mounted on a PC board;

FIG. 8 shows a side sectional view of a typical reed switch and its relative position with respect to the permanent magnet; and FIG. 9 shows the magnetic field generated by the magnet to activate one of the switches.

Description of the Preferred Embodiment

As can be seen in FIG. 1, an electric toothbrush, according to this invention, comprises an elongated preferably cylindrical plastic housing 10 with essentially two openings 12, and 14 located at the opposite ends of the housing.

Opening 12 is provided as an entry hole for the two-conductor wire 16 which supplies power to the motor. Preferably wire 16 is connected to a miniature transformer (not shown) used to step down standard house-current (i.e. 110 or 220 vac) to a low voltage such as 15 vac. The second opening 14 is provided to allow a shaft 18 to extend outward as shown, so that a toothbrush head 20 thereon. Within the housing there are three axially spaced assemblies 22, 24 and 26. Assemblies 22 and 26 are provided to rotatably support an axle (not shown) which terminates with shaft 18. Also mounted on the axle is a cylindrical magnet formed of two axially extending equal portions with opposite magnetization, each having a semicircular cross-section. Assembly 24 contains two coils positioned so that when they are energized their magnetic field is oriented perpendicularly to said axle.

Assembly 22 also contains a biasing spring which urges the axle towards a preset angular position. As described in the above defined patent application, the spring, axle and magnet define a mechanical oscillating system with a frequency of oscillation which is equal to, or slightly less than the electric supply frequency. Therefore when electric energy is supplied to the coils of assembly 24, the axle and shaft 18 rotate or oscillate angularly back and forth with respect to the preset (or dead) position defined by the spring.

A similar device to the one shown in FIG. 1 may be used as a face massaging and/or skin treatment device. For this purpose, instead of toothbrush head 20, a pad or a massaging head 28 may be used, as shown in FIG. 2. Preferably the massaging head 28 comprises a stem 30 adapted for mounting on shaft 18 of the device and a disk-shaped member 32 oriented at an angle with respect to said stem 28 so that its top surface 34 could be applied to a person's face skin and tissue. Preferably the whole head 28 is molded out of a plastic material for a pleasing aesthetic effect. In order to increase the effectiveness of the head, a plurality of relatively hard plastic balls 36 are rotatably embedded or captured by surface 34 as shown.

The operation of the device is controlled by a switching element 38 which is preferably slidably mounted on the housing 10 so that the device can be held and operated with a single hand.

Because the motor of the device is mechanically tuned to the power supply frequency, its rate of operation, i.e. the number of oscillations per second is constant and does not change with the load or current. It has been found that the angle of operation, i.e. the maximum amplitude of each oscillation of shaft 18 can be varied by varying the current to the motor. This is accomplished as shown in FIG. 3 by placing a number of switches and resistors in series with motor 40. In the schematic of FIG. 3 three separate switches are shown for a LOW (Lo), MEDIUM (Med) or HIGH (Hi) setting. For the high setting, switch 42 is used. In this position the motor is supplied with the maximum current to obtain the maximum angle of operation A as shown on FIG. 4. For a medium setting switch 44 is closed thereby placing a first resistor 46 in series with the motor. This resistor reduces the current to motor 40 consequently reducing the angle of operation to B as shown in FIG. 4. Finally for a low setting switch 48 is closed thereby placing first resistor 46 and second resistor 50 in series with motor 40 to further limit the operation of the toothbrush to angle C.

The torque generated by the motor is proportional to the angle of operation so that maximum torque is produced at Hi setting and minimum torque is produced at Lo setting. By varying the settings between Hi and Lo setting the amount of pressure that can be applied with the device is also varied. Thus at the Hi setting more vigorous brushing or massaging action is obtained than at lower settings. Importantly as the pressure on the shaft, i.e. the resistance to the shaft's movement is increased, the angle of rotation of the shaft decreases until a threshold level is reached beyond which the shaft stops oscillating but the motor is not damaged. Thus an automatic overload protection mechanism is built into the device which insures that if the device is operated improperly (for example by applying undue pressure to it) neither the user nor the device will be injured.

All the switching functions described above and in FIG. 3 are performed by a switching assembly 38 and other elements more fully described below. The switching element 38 disposed on the housing and a P.C. board 52 disposed on assembly 26 as shown. The actual switches 42, 44, 48 are mounted on the P.C. board and preferably there is no physical contact between the switching element 38 and the switches. Preferably switches 42, 44, 48 are reed switches which are activated by a magnet imbedded in switching element 38 described more fully below.

The switching element 38 is shown in FIGS. 5 and 6 and it comprises a handle 54 which has an outer surface 56 with a plurality of transversal grooves 58 provided so that handle 54 can be moved easily longitudinally with respect to the device. A generally rectangular cavity 60 is formed in the housing 10 extending in parallel with its longitudinal axis. On its two long sides the cavity has slightly overhanging lips 62 as shown. A square slug 64 is disposed in the cavity with a width which is substantially equal to the width of the cavity. Thus slug is captured in the cavity by lips 62 so that it may slide longitudinally without falling out. Along lips 62 there are a plurality of indentations 66 and slug 62 has at least one flexible knob 68 adapted to fit into said indentations to provide fixed positions for the slug as it is moved along the cavity. Slug 62 also has two holes 70 arranged on its top surface as shown and handle 54 has two protrusions 72 which are complementary to said holes 70 so that the handle 54 is affixed to slug 64 and housing 10 by positioning said handle on top of the slug so that the protrusion 72 are disposed above holes 70, and then pressing down on the handle so that an interference fit is formed between the protrusions 72 and slug 64. Thus handle 54 is slidably affixed to the housing so that as it is moved longitudinally it moves slug 64 with it.

As can be best seen in FIG. 5 a magnet 74 is imbedded in the slug, preferably close to the bottom wall 76 of cavity 60.

As previously mentioned, switching element 38 moves axially along housing 10. For ease of assembly, electrical safety, and optimum life expectancy, switches 42, 46, 48 are reed switches physically spaced away from the element 38, and are activated by magnet 74. The arrangement of these switches and the cooperation between the switches and the magnet shall now be described in conjunction with FIGS. 7, 8 and 9.

Ergonomically, the total axial stroke of the switching assembly should be in the range of 12–15 mm so that it can be thumb-activated while the device is held in one hand. Each step of the stroke should be in the range of 3–4 mm. It has been found that a device meeting these criteria can be operated by a child or an adult with ease. The reed switches must be able to open and close completely in accordance with the operation described above and in FIG. 3. This is especially true for the left-most position of the switching assembly in which all the switches must be open. It shall become apparent from the following description that all these criteria are met by the present invention.

As shown in FIG. 7, reed switches 42, 46 and 48 are mounted side-by-side in close proximity to each other on printed circuit board 52. Each reed switch comprises (as shown in FIG. 8) a generally cylindrical housing 76, and two axially extending conductors 78 and 80. The two conductors overlap but are separated by a contact gap 82. A magnetic field applied transversally to the reed switch forces the conductors to close the gap and make electrical contact with each other. The strength of the magnetic field required to close the conductors depends on the overall length of the switch and the flexibility of the conductors. Generally 15 mm long reed switches, commercially available, have been found to be optimal for the present invention.

The magnet 74 is preferably made of anisotropic material to produce a high magnetic field intensity at an operating distance of about 3mm and to insure that the magnetic flux lines are substantially perpendicular to the reed switches. Otherwise a hysteresis effects may produce undesirable operation of the reed swithces.

If the contact zone or gap 82 of a reed switch is aligned perfectly with the axis of symmetry of magnet 74, the switch might not operate because both conductors 76, 78 would be magnetized to the same polarity, thereby repelling rather than attracting each other. Therefore preferably the reed switches are positioned so that their contact areas or gaps 82 are offset from the axis of the magnet and switch assembly as shown in FIGS. 7 and 8. For example, 15mm reed switches are available which have a gap offset by 3.5mm as shown in FIG. 8. These reed switches can be mounted on the printed circuit with their centers shifted axially by 1mm so that the net spacing between the axes of the reed switch gaps and the magnet is 2.5mm as shown. The longitudinal axes of the switches form an angle of 40°–70° with the direction of movement of slug 64 and the longitudinal axis of housing 10. Preferably, this angle is about 50°, as shown in FIG. 7. If symmetrical reed switches would be used, the size of the printed circuit board would have to be increased to accommodate the offset switches, increasing the overall thickness of housing 10. Of course an alternate arrangement may be devised in which the reed switches are mounted symmetrically and the magnet 74 is offset.

The reed switches are activated as follows. When the device is assembled and slug 64 is in the left most, or OFF position, magnet 74 is too far away from the reed switches and therefore none of them are closed. As the slug 64 is moved right to the LOW setting, magnet 74 is disposed above and closes switch 42. Similarly at the MEDIUM and HIGH settings the magnet closes switches 44 and 48 respectively.

By using the above-described members and arrangement, a slim, compact hygienic apparatus is achieved with adjustable operating angle and torque. The following settings are suggested for a typical apparatus by selecting appropriate values for resistors 46 and 50.

| SETTING | MECHANICAL OUTPUT POWER (W) | ANGLE OF OPERATION |
| --- | --- | --- |
| 1 | 0.6 | 5–8° |
| 2 | 1.2 | 10–13° |
| 3 | 1.8 | 15–19° |

Obviously numerous modifications could be made to the described device without departing from the scope of the invention as defined in the appended claims.

What is claimed is:

1. An electric hygienic device operated from an a.c. electric supply having a frequency comprising:
    a tubular housing with a longitudinal axis;
    an electric motor disposed within said housing with a shaft which oscillates at an operative angle, the rate of oscillation of the shaft being dependent only on said frequency; and
    a switch assembly for varying said operative angle by varying the power supplied to said motor, said switch assembly including;
    a switching element slidably mounted on said housing for movement in parallel with said longitudinal axis and including a magnet; and
    a plurality of reed switches disposed within said housing, said reed switches each having a major axis, said reed switches being positioned adjacent to each other with said axes in parallel, and at an angle of 40°–70° with respect to said longitudinal axis said switching element being constructed and arranged to selectively activate said reed switches as it moves.

2. The device of claim 1 further comprising resistors selectively switched in series with said motor by said switching assembly.

3. The device of claim 2 wherein said reed switches are in series with said resistors and mounted on said motor, and wherein said switch assembly comprises a permanent magnet.

4. The device of claim 3 wherein said reed switches are coplanar and said magnet is oriented and positioned to generate a magnetic flux perpendicular to the plane of said reed switches.

5. The device of claim 4 wherein said magnet is made of an anisotropic material.

6. The device of claim 4 wherein said first predetermined angle is about 50°.

7. The device of claim 4 wherein said magnet has an axis of symmetry and said reed switches have gaps which are offset from said axis of symmetry by a predetermined amount.

8. The device of claim 7 wherein said reed switches have two opposed ends and said gaps are closer to one of said opposed ends.

\* \* \* \* \*

UNITED STATES PATENT AND TRADEMARK OFFICE
CERTIFICATE OF CORRECTION

PATENT NO. : 4,595,850

DATED : June 17, 1986

INVENTOR(S) : Philippe Guy E. Woog

It is certified that error appears in the above-identified patent and that said Letters Patent is hereby corrected as shown below:

Column 2, line 41, after "head 20" insert --can be mounted--

Column 5, line 15, after "switches" insert --thereby--.

Signed and Sealed this

Twenty-first Day of October, 1986

[SEAL]

Attest:

DONALD J. QUIGG

Attesting Officer     Commissioner of Patents and Trademarks